United States Patent
Lebok et al.

(12)
(10) Patent No.: US 6,277,182 B1
(45) Date of Patent: Aug. 21, 2001

(54) PIGMENT-CONTAINING OIL-BASED GEL MATERIALS

(75) Inventors: Simona Lebok; Claudia Zarling, both of Nurnberg; Wolfgang Winkler, Lauf, all of (DE)

(73) Assignee: Schwan-STABILO Cosmetics GmbH & Co., Heroldsberg (DE)

(*) Notice: Subject to any disclaimer, the term of this patent is extended or adjusted under 35 U.S.C. 154(b) by 0 days.

(21) Appl. No.: 09/521,157

(22) Filed: Mar. 8, 2000

(30) Foreign Application Priority Data

Mar. 11, 1999 (DE) .............................. 199 10 870

(51) Int. Cl.⁷ .................................... C09D 11/00
(52) U.S. Cl. .................... 106/31.11; 106/31.12; 106/243
(58) Field of Search ............ 106/31.11, 31.12, 106/266, 268, 243, 245

(56) References Cited

U.S. PATENT DOCUMENTS

| | | | |
|---|---|---|---|
| 4,425,328 | | 1/1984 | Nabial .................................. 424/68 |
| 5,340,386 | | 8/1994 | Vincent et al. ................... 106/31.94 |
| 5,552,136 | | 9/1996 | Motley ................................ 424/68 |
| 5,939,082 | * | 8/1999 | Oblong et al. ..................... 424/401 |
| 5,976,514 | * | 11/1999 | Guskey et al. ...................... 424/65 |
| 6,042,815 | * | 3/2000 | Kellner et al. ..................... 424/63 |
| 6,083,493 | * | 7/2000 | Swaile ................................ 424/65 |
| 6,162,421 | * | 12/2000 | Ordino et al. ..................... 424/64 |

* cited by examiner

Primary Examiner—C. Melissa Koslow
Assistant Examiner—Veronica F. Faison
(74) Attorney, Agent, or Firm—Bachman & LaPointe, P.C.

(57) ABSTRACT

A pigment-containing oil-based gel material which contains 0.1 to 25% by weight of a hydroxy-fatty acid having 10 to 20 C atoms, 0.1 to 30% by weight of $C_{30-45}$-alkylmethicone, 1 to 70% by weight of an oil component and 0.1 to 50% by weight of pigments is described.

24 Claims, No Drawings

PIGMENT-CONTAINING OIL-BASED GEL MATERIALS

BACKGROUND OF THE INVENTION

The invention relates to pigment-containing oil-based gel materials, colored pencils containing them and a process for the production of colored pencils.

Pigment-containing oil-based gel materials are dispersed systems which consist of a skeleton of the gel-forming component with an oil component incorporated therein. The gel material furthermore contains pigments for coloring. Such materials are suitable for applying colors in many areas. Suitable principal fields of use for pigmented gel materials are in colored materials for drawing and painting and the area of decorative cosmetics, where they can be used in many forms, inter alia for make-up, creamy eye shadows, lipsticks and eyeliner and eyebrow pencils. In particular, such pigment-containing gel materials can be used for producing cosmetic pencils or sticks.

Materials used for drawing, painting or make-up should be capable of being easily applied but should be well retained after application and should as far as possible be water-resistant, in the case of cosmetics pencils also tear-resistant, and transfer-resistant, i.e. should not stain other surfaces and articles and should not bleed from the area of application.

Known formulations for pencils or sticks are based on a mixture of waxes and oils which is colored with pigments. Thus, pencil or stick formulations composed of natural or mineral waxes, natural or synthetic oils or mineral oils and conventional additives, such as lanolin or lanolin derivatives, are described, for example, for lipsticks or eye shadow pencils. As a rule, these formulations are thixotropic systems which liquefy under the shear forces occurring during application and thus permit gentle application.

In the area of cosmetics, gel-like mixtures have predominantly been used to date for deodorant and antiperspirant sticks. They contain a considerable proportion of volatile silicone oils, such as cyclomethicone or dimethicone, or hydrocarbon oils, such as isoparaffin. These gels have the advantage that they can be readily applied but the disadvantage that they have no mechanical load capacity. For deodorant sticks, the advantage of easy application predominates whereas, owing to the shape of the sticks, stability is not so important. Deodorant sticks have a large diameter in relation to their length and the requirements with respect to the strength are not very high owing to the composition of the sticks. It has been found that materials which are suitable as deodorant sticks can be shaped into relatively thin leads only to a limited extent and in particular, since the material is too soft and unstructured, can be removed from the mold only with great difficulties or not at all.

Attempts have also been made to prepare oleogels containing candelilla wax and to shape them into leads. Owing to its gloss, candelilla wax is popular for lipsticks and eye shadow pencils. However, it has been found that the known oleogels have an insufficient oil-binding capacity, so that phase separation occurs and the oil contained in the material migrates into the environment. This impairs the aesthetic appearance of the pencil. Moreover, the loss of oil results in the sticks losing their elasticity and becoming brittle. In addition, it has been found that, as a result of the diffusion, evaporation or migration of the oil, the leads produced from the material shrink to such an extent that, when an attempt is made to produce colored pencils, leads inserted into wood slip out of the wood sleeves after a short time.

It is an object of the present invention to eliminate the disadvantages described above and to provide an oil-based gel material which has a high oil-binding capacity and which is suitable for being processed to give leads for pencils, in particular cosmetic pencils. It is a further an object of the invention to provide a material whose texture is stable and which as far as possible is water- and tear-resistant and is transfer-resistant, i.e. does not stain surfaces or articles after application. In addition, the application properties of the material should be good, i.e. it should be capable of being applied up to about 40° C. without deforming or smearing but should also not be too hard. For cosmetics pencils, it is moreover desirable for the gel material to be composed of only a few, cosmetically acceptable components. Moreover, the material should be capable of being shaped by casting or extrusion.

SUMMARY OF THE INVENTION

The foregoing objects are achieved by the present invention by providing a pigmented oil-based gel material which contains 0.1 to 25% by weight of a hydroxy-fatty acid having 10 to 20 C atoms, 0.1 to 30% by weight of $C_{30-45}$-alkylmethicone, 1 to 70% by weight of an oil component and 0.1 to 50% by weight of pigments.

DETAILED DESCRIPTION

Surprisingly, it has been found that a combination of a hydroxy-fatty acid with C30-45-alkylmethicone forms an outstanding matrix for binding oil components and gives a gel material which has excellent properties and can be very readily shaped by extrusion and casting. The four main components give a structured material which shows no phase separation even under thermal stress up to 45° C. $C_{30-45}$-alkylmethicone, together with the hydroxy-fatty acid, forms a stable matrix which permanently and strongly binds the oil and the pigments. In addition, the material is given excellent thermal stability. This makes it possible to process the material at elevated temperatures and to store it without cooling.

One component, essential to the invention, of the gel material is the hydroxy-fatty acid, which has a gel-forming effect on the structure. It is a fatty acid having 10 to 20 C atoms, which carries at least one hydroxyl group, preferably in the chain and not as a terminal group. It is preferably a $C_{16}$-hydroxy-fatty acid, and 12-hydroxystearic acid is particularly preferably used owing to its ready availability. The hydroxy-fatty acid is contained in the material in a proportion of 0.1 to 25% by weight, based on the material formed from pigment, methicone, oil and fatty acid. Below 0.1% by weight, no effect is detectable. A proportion of more than 25% by weight results in the proportion of the other structure-forming components decreasing to such an extent that a stable structure is difficult to obtain. Preferably, the hydroxy-fatty acid is used in an amount of 1 to 20% by weight. Particularly good results are obtained with a proportion of 2 to 15% by weight.

The other component important for the structure is $C_{30-45}$-alkylmethicone. "$C_{30-45}$-alkylmethicone" is the INCI name for a silicone resin which comprises long-chain alkyl radicals and has waxy properties and is commercially available under this name. This component contributes substantially to the advantages achieved with the gel material according to the invention. It has been found that, when other silicone resins, e.g. stearyl-dimethicone, or natural waxes, e.g. candelilla wax, are used, the oil-binding capacity is not sufficient for keeping oil components in a stable structure, and is also not capable of doing so in combination with a hydroxy-fatty acid. $C_{30-45}$-alkylmethicone is present in the gel material according to the invention in a proportion of 0.1 to 30% by weight. With an amount of less than 0.1% by weight, the advantageous properties cannot be achieved. The addition of more than 30% by weight leads to hard, brittle materials having undesired application properties. The $C_{30-45}$-alkylmethicone is preferably used in an amount of 1 to 30% by weight, particularly good results being obtained with a proportion of 5 to 20% by weight.

A further essential ingredient of the gel material according to the invention is the oil component. The oil component may comprise vegetable, animal, mineral or synthetic fat and/or oil and wax. Thus, inter alia, oils, fats, fatty oils, paraffins and vaseline are suitable for the present invention. All of these components are bound by the combination, according to the invention, of hydroxy-fatty acid and $C_{30-45}$-alkylmethicone. The more viscous the oil component, the smaller should the amount used be, in order to obtain the desired properties in the case of the finished composition. Natural and synthetic oils, mineral oils, lanolin and lanolin derivatives, isoparaffins, nonvolatile or volatile silicone oils, such as cyclomethicone or dimethicone, and mixtures thereof may be mentioned as examples of the oil component. Fatty oils used are in particular vegetable oils, e.g. hydrogenated vegetable oils.

The oil is used in a proportion of 1 to 70% by weight. With less than 1% by weight, the material becomes too viscous. If the proportion of the oil is too high, i.e. is above 70%, undesirable loss of oil may occur. The desired viscosity of the material can be established in a suitable manner through the choice of the type and amount of the oil component, by means of a few routine tests.

A part of the oil component can also be wax. Natural and mineral waxes as well as synthetic waxes, e.g. silicone waxes, are suitable for this purpose. Mixtures of oily and waxy substances are preferably used as the oil component. If the gel material is to be used for producing cosmetics pencils, a wax customary in cosmetics is preferably used, such as beeswax, carnauba wax, candelilla wax, Japan wax, montan wax, microcrystalline wax or a mixture of these waxes. Owing to its gloss on application, candelilla wax is particularly preferred for a gel material which is intended for producing decorative cosmetics. Volatile and/or nonvolatile oils are preferably used as the oil fraction for this purpose. A mixture of volatile silicone oils, such as cyclomethicone or dimethicone, with waxes, paraffins or fatty oils is particularly preferred. The volatile silicone oils on the one hand facilitate the application of the gel material and on the other hand substantially increase the stability and water resistance of the applied layer, the wind-burn effect being avoided with a suitable choice.

The chosen proportion of wax is dependent on the viscosity of the gel material and the desired viscosity properties of the finished product. The proportion of wax in the total composition is preferably 0.1 to 25% by weight.

The fourth component, essential to the invention, of the gel material is a pigment or a pigment mixture. The substances usually used for pigmented materials are used here. Examples of suitable pigments are iron oxides, titanium dioxide, mica, talc, color lakes and mixtures thereof Furthermore, lamellar metal powders or glitter, for example in the form of PET films or aluminum lamellae having a colored coating, may be contained as gloss pigments. The pigments used for decorative cosmetics are preferably employed. The content of the pigment or of the pigment mixture in the gel material according to the invention is in a range from 0.1 to 50% by weight, preferably 1 to 40% by weight, depending on the color intensity of the pigment used. An amount of 5 to 30% by weight is particularly preferred.

In addition to the components mentioned, the gel material according to the invention may contain further additives and auxiliaries which are usually used for such materials. Examples are fillers, thickeners, humectants, emulsifiers, perfumes, aromas, antioxidants and preservatives, which may be used in the amounts usually used.

The gel material according to the invention is preferably anhydrous, so that preservatives are not absolutely essential since microorganisms cannot grow under these conditions. Use of antioxidants is advisable, in particular if the oil component contains unsaturated fatty acids, in order to prevent the material from becoming rancid or spoiling.

The total amount of additives should not exceed 45% by weight and preferably, together with the amount of pigments, should be in a range from 0.1 to 50% by weight, preferably 1 to 40% by weight, and particularly preferably in a range from 5 to 35% by weight.

The pigmented oil-based gel material according to the invention can be brought into any desired shapes. It is particularly preferably shaped into leads and then used in the form of pencils. A further advantage of the gel material according to the invention is that it can be shaped by casting and extrusion methods. The gel material according to the invention is particularly preferably processed to give colored pencils and cosmetics pencils or sticks. The leads produced and having a gel texture have the advantage that they can be readily applied without becoming deformed or smearing.

The present invention furthermore relates to a colored pencil which comprises a sleeve of wood or plastic with a lead embedded therein and comprising a pigmented oil-based gel material. The colored pencil is preferably a cosmetics pencil and is particularly preferably an eye shadow pencil, lipliner pencil, eyeliner pencil, kohl pencil or eyebrow pencil.

The colored pencil according to the invention is produced by melting the pigmented gel material prepared according to the invention and pouring it into a sleeve blank or by extruding the pigmented gel material and placing or inserting the resulting molding in a sleeve blank.

Owing to the improved oil-binding capacity and a high thermal stability, the leads produced from the pigmented oil-based gel material according to the invention have positive properties. They can be used up to 40° C. The leads have sufficient hardness and elasticity and can be readily sharpened.

The invention furthermore relates to a process for the production of pencils using the gel material according to the invention, as defined in claims 18 and 19.

Owing to the stability of the gel material, it can be processed, for example melted and shaped, without problems to give leads, including very thin leads. Since on the one hand the gel material is thermally stable and on the other hand the shaped leads have sufficient strength, to produce the pencils either the gel material according to the invention can be cast directly in sleeve blanks or in casting molds mounted on a rotary mechanism, which are then further processed in a manner known per se to give pencils, or leads can first be produced in one operation by casting or extrusion and can then be inserted into the desired sleeve or into a rotary mechanism. Both variants have advantages, and the most suitable embodiment can be selected for the respective purpose.

According to one embodiment, the pigmented gel material is preferably shaped by casting or extrusion for the production of leads. Shaping by the casting method is preferred since in this case the material can be cast directly in the sleeve blank intended for receiving the lead, without having to be removed from the mold again and further processed. The blank is then further processed in a manner known per se to give a lead pencil. In this way, the waste can be kept small.

In another preferred embodiment, a lead is shaped from the pigmented gel material according to the invention by extrusion or casting and is inserted into a rotary mechanism after removal from the mold. Even without support, the gel material according to the invention has such a stable structure that it can be extended and retracted by turning in a rotary mechanism without breaking off It is therefore also very suitable for producing rotary sticks.

The invention is illustrated by the following examples.

Example 1

Eyeliner

A gel material was prepared from the following components (the raw material are stated with INCI names):

| | |
|---|---|
| Pigments | 30.000% (w/w) |
| Caprylic capric triglyceride | 42.000% (w/w) |
| Butyl stearate | 5.000% (w/w) |
| $C_{30-45}$-Alkyl methicone | 10.000% (w/w) |
| 12-Hydroxystearic acid | 10.000% (w/w) |
| Hydrogenated vegetable oil | 3.000% (w/w) |

All components, except for the pigments, were heated to 90° C. and melted, and the pigments were then added to the molten material. Thereafter, the material was homogenized, deaerated, poured at 90° C. into prepared sleeve blanks and allowed to cool. The pencils obtained were further processed by customary methods. The eyeliners obtained could be readily applied and gave a water-resistant and tear-resistant coating.

Example 2

Eye Shadow

A gel material was prepared from the following components:

| | |
|---|---|
| Pigments | 19.500% (w/w) |
| Vegetable oil | 20.000% (w/w) |
| Jojoba oil | 7.000% (w/w) |
| Cyclomethicone | 30.500% (w/w) |
| $C_{30-45}$-Alkyl methicone | 13.500% (w/w) |
| 12-Hydroxystearic acid | 7.500% (w/w) |
| Candelilla wax | 2.000% (w/w) |

All components, except for pigments and cyclomethicone, were heated to 80° C. and melted, and the pigments were then added to the molten material. Thereafter, the material was homogenized and deaerated. The cyclomethicone was then added and thoroughly mixed in. Thereafter, the material was poured at 80° C. into prepared sleeve blanks and allowed to cool. The pencils obtained could be very readily applied and gave a glossy, abrasion-resistant coating.

Example 3

Lipliner

A gel material was prepared from the following components:

| | |
|---|---|
| Pigments | 20.000% (w/w) |
| Caprylic capric triglyceride | 30.000% (w/w) |
| Hydrogenated vegetable oil | 12.000% (w/w) |
| $C_{3-045}$-Alkyl methicone | 10.000% (w/w) |
| 12-Hydroxystearic acid | 12.000% (w/w) |
| Microcrystalline wax | 3.000% (w/w) |
| Castor oil | 13.000% (w/w) |

All components, except for the pigments, were heated to 80° C. and melted, and the pigments were then added to the molten material. The material was homogenized and deaerated. Thereafter, the material was poured at 80° C. into suitable molds and cooled. The shaped leads were removed from the mold and inserted into sleeve blanks, glued, and further processed in a customary manner. The pencils obtained could be readily sharpened, and the pencils obtained were suitable for application in exact contours, which was stable and had an intense color.

What is claimed is:

1. A pigment-containing oil-based gel material comprising 0.1 to 25% by weight of a hydroxy-fatty acid having 10 to 20 C atoms, 0.1 to 30% by weight of $C_{30-45}$-alkyluethicone, 1 to 70% by weight of an oil component and 0.1 to 50% by weight of pigments.

2. The gel material as claimed in claim 1, wherein the hydroxy-fatty acid is 12-hydroxystearic acid.

3. The gel material as claimed in claim 1, which contains 0.5 to 20% by weight of hydroxy-fatty acid.

4. The gel material as claimed in claim 1, which contains 1 to 15% by weight of hydroxy-fatty acid.

5. The gel material as claimed in claim 1, which contains 1 to 25% by weight of $C_{30-45}$-alkyl-methicone.

6. The gel material as claimed in claim 1, which contains 5 to 20% by weight of $C_{30}45$-alkyl-methicone.

7. The gel material as claimed in claim 1, wherein the oil component is selected from the group consisting of vegetable, animal, mineral, synthetic, nonvolatile silicone oil, volatile silicone oil and wax.

8. The gel material as claimed in claim 1, which contains wax in a proportion of 0.1 to 25% by weight, based on the weight of the composition.

9. The gel material as claimed in claim 8, wherein the wax is selected from the group consisting of natural, mineral and synthetic wax.

10. The gel material as claimed in claim 1, which contains a mixture of oil and wax as the oil component.

11. The gel material as claimed in claim 10, wherein the wax is selected from the group consisting of beeswax, carnauba wax, candelilla wax, Japan wax, montan wax, microcrystalline wax and mixtures thereof.

12. The gel material as claimed in claim 1, which contains fillers in a proportion of 0.1 to 45% by weight, based on the weight of the composition.

13. The gel material as claimed in claim 1, which contains pigments in an amount of 1 to 40% by weight.

14. The gel material as claimed in claim 1, which contains pigments in an amount of 5 to 30% by weight.

15. The gel material as claimed in claim 13, wherein the pigments are selected from the group consisting of iron oxides, titanium dioxide, mica, talc, colored lakes, gloss pigments, and mixtures thereof.

16. The gel material as claimed in claim 1, which is present in the form of a cast or extruded lead.

17. A colored pencil comprising a lead of a gel material as claimed in claim 1, which is surrounded by a sleeve blank of material.

18. A colored pencil according to claim 17 wherein the material is selected from wood or plastic.

19. A colored pencil comprising a lead of a gel material as claimed in claim 17, which is inserted into the rotary mechanism of a rotary pencil.

20. The colored pencil as claimed in claim 15, wherein the pencil is a cosmetics pencil.

21. The colored pencil as claimed in claim 20, wherein the pencil is an eye shadow pencil, eyeliner pencil, kohl pencil, eyebrow pencil or lipliner pencil.

22. A process for producing a colored pencil, wherein a gel material as claimed in claim 16, is melted and is then poured into a blank sleeve material for a lead pencil and then processed to give a pencil.

23. A process for producing a colored pencil, wherein, for the production of a rotary pencil, a gel material as claimed in claim 1, is melted and is poured into a mold mounted on a rotary mechanism.

24. A process for producing a colored pencil, wherein, for the production of a rotary pencil, a gel material as claimed in claim 1, is melted and is poured into a casting mold and the lead formed is inserted into the rotary mechanism of a rotary pencil after removal from the mold.

* * * * *

UNITED STATES PATENT AND TRADEMARK OFFICE
CERTIFICATE OF CORRECTION

PATENT NO. : 6,277,182 B1
DATED : August 21, 2001
INVENTOR(S) : Simona Lebok et al.

Page 1 of 1

It is certified that error appears in the above-identified patent and that said Letters Patent is hereby corrected as shown below:

Column 2,
Line 29, change "C30-45-alkylmethicone" to -- $C_{30\text{-}45}$-alkylmethicone --.

Column 3,
Line 62, insert -- . -- after "thereof".

Column 5,
Line 16, insert -- . -- after "off".

Column 6,
Line 4 of the example, change "$C_{3\text{-}045}$-Alkyl" to -- $C_{30\text{-}45}$-alkyl --.
Line 28, change "$C_{30\text{-}45}$-alkyluethicone" to -- $C_{30\text{-}45}$-alkylmethicone --.
Line 39, change "$C_{30}45$" to -- $C_{30\text{-}45}$ --.

Signed and Sealed this

Nineteenth Day of March, 2002

Attest:

JAMES E. ROGAN
Director of the United States Patent and Trademark Office

Attesting Officer